United States Patent
Kawasaki et al.

(10) Patent No.: US 7,463,916 B2
(45) Date of Patent: Dec. 9, 2008

(54) OPTICAL MEASUREMENT APPARATUS FOR LIVING BODY

(75) Inventors: Shingo Kawasaki, Chiba (JP); Eiju Watanabe, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 1387 days.

(21) Appl. No.: 10/398,185

(22) PCT Filed: Oct. 16, 2001

(86) PCT No.: PCT/JP01/09064

§ 371 (c)(1),
(2), (4) Date: Apr. 2, 2003

(87) PCT Pub. No.: WO02/32317

PCT Pub. Date: Apr. 25, 2002

(65) Prior Publication Data

US 2004/0039267 A1 Feb. 26, 2004

(30) Foreign Application Priority Data

Oct. 16, 2000 (JP) ............................. 2000-315115

(51) Int. Cl.
*A61B 5/1455* (2006.01)
(52) U.S. Cl. .................... 600/310; 600/473; 600/476
(58) Field of Classification Search ................. 600/310, 600/322, 323, 340, 473, 476
See application file for complete search history.

(56) References Cited

U.S. PATENT DOCUMENTS 5,803,909 A 9/1998 Maki
6,397,099 B1 * 5/2002 Chance ...................... 600/323

FOREIGN PATENT DOCUMENTS

| GB | 2 311 854 | 10/1997 |
| JP | 9-98972 | 4/1997 |
| JP | 9-135825 | 5/1997 |
| JP | 2000-237194 | 9/2000 |
| WO | WO 00/40841 | 7/2000 |

* cited by examiner

*Primary Examiner*—Eric F Winakur
(74) *Attorney, Agent, or Firm*—Antonelli, Terry, Stout & Kraus, LLP.

(57) ABSTRACT

An optical measurement apparatus for a living body having light transmitting elements for transmitting light to a plurality of positions in areas to be examined within a living body detects light which has been transmitted by the light transmitting elements after passing through the living body at a plurality of positions in the examination area; applies to the living body a load to which the living body responds; calculates signals representing an intensity change of the transillumination detected by the detecting the light at the measuring points based on the positional relation between each light transmitting position and light detecting position when a load is applied to the living body and when a load is not applied; calculates time variations of one signal among two signals calculated at the measuring points based on said positional relation; and displays graphs of the above-calculated signals in correspondence with said positional relation.

17 Claims, 8 Drawing Sheets

OPTICAL MEASUREMENT APPARATUS FOR LIVING BODY

FIELD OF THE INVENTION

The present invention relates in general to an optical measurement apparatus for examination of a living body; and, more particularly, the invention relates to a technique that is effective in observing areas where there is a response by the object to be examined to outside stimulation.

BACKGROUND OF THE INVENTION

In recent years, an optical measurement apparatus for examination of a living body has been developed, by which the functions of tissue in a living body are observed by transmitting laser light to the interior of the living body and detecting signals generated due to interaction between the laser light and hemoglobin in the blood flow within the living body. Such an optical measurement apparatus for the living body is disclosed, for example, in Japanese Patent Laid-open Publication JP-A-9-98972 (hereinafter referred to as "document 1").

The optical measurement apparatus for the living body, as mentioned in the above-reference patent publication, is constituted of modulated semiconductor laser devices for generating light having various modulation frequencies; light-transmitting optical fibers for guiding the light generated by the semiconductor laser devices to transmit light to a plurality of positions; detecting optical fibers for collecting the light which has passed through the living body (hereinafter referred to as "living-body transillumination") and for guiding it to photodiodes; a fixing member for fixing the tips of the light-transmitting optical fibers and the detecting optical fibers to predetermined positions on the living body; lock-in amplifiers for separating electrical signals of the optical intensity of the living-body transillumination which are output from the photodiodes (hereinafter referred to as "living-body transillumination intensity signals"), according to wavelength and measurement position; an A/D converter for converting the outputs of the lock-in amplifiers into digital signals; an input/output unit having an image generation unit for generating an image of the living-body transillumination intensity signal (a topography image), corresponding to variations of hemoglobin concentration at each measuring point from the living-body transillumination intensity signals, after A/D conversion; and an image display unit for inputting an operation instruction for the apparatus and displaying the living-body transillumination intensity signal image.

In this specification, the term "transillumination" hereinafter means any kind of light, including transmitted light, reflected light, and scattered light, which is generated at a light source and detected at a detector (a light detector) after interacting with the living body.

In a measurement using the conventional optical measurement apparatus for the living body as described above, the fixing member is first placed on the living body, and the light-transmitting optical fibers and the detecting optical fibers, supported by a probe holder provided to the fixing member, are applied to predetermined positions on the living body. Then, in a preliminary measurement, for example, plural measurements of 10 seconds each, living-body transillumination intensity signals in the resting state are measured, and the measured values are averaged to calculate hemoglobin concentration in measured areas of the living body in the resting state. Next, the living-body transillumination intensity signals are measured in the state where stimulation is applied to the living body.

Then, relative variations of oxygenated hemoglobin concentration and relative variations of deoxygenated hemoglobin concentration are calculated at each measuring point from the measured living-body transillumination intensity signals in the resting state and the measured living-body transillumination intensity signals in the state where stimulation is applied. An image of the living-body transillumination intensity signal is generated from the relative variations of oxygenated hemoglobin concentration, the relative variations of deoxygenated hemoglobin concentration, and the relative variations of total hemoglobin concentration, which is the sum of the relative variations of oxygenated hemoglobin concentration and deoxygenated hemoglobin concentration, and this image is displayed.

To describe in more detail the mode of image display in the conventional optical measurement apparatus for living body, relative variations of oxygenated hemoglobin concentration, relative variations of deoxygenated hemoglobin concentration, and relative variations of the total hemoglobin concentration are calculated at each measuring point from the living-body transillumination intensity signal acquired at a measuring point (a position to be measured), which is the area between a pair of elements, consisting of the light-transmitting optical fiber and the detecting optical fiber, which are adjacently placed. The relative variations of oxygenated hemoglobin concentration and the relative variations of deoxygenated hemoglobin for each pixel are calculated by spline interpolation, and the like, from the relative variations of oxygenated hemoglobin concentration and the relative variations of deoxygenated hemoglobin concentration obtained at each measuring point. When the result thereof is displayed as an image, the area where the variation is minimum, among those relative variations, is provided with blue hue, the area where the variation is maximum is provided with red hue, and areas between them are provided with medium hues between blue and red in accordance with their variation. The area where the variation of hemoglobin concentration is maximum represents the area which has been activated by the application of stimulation. In this manner, the area which has been activated by stimulation, that is, the functioning area of the living body, is identified by the variations of hemoglobin concentration in the measuring area.

After considering the above-described conventional technique, the present inventor has found a problem. That is, to take the therapy of epilepsy as an example, therapy in which the focal point of epilepsy is identified and is excised requires not only accurate identification of the focal point of epilepsy, but also accurate identification of positions of a speech function area (the "speech area"), a visual function area ("the optic area") and the like. The reason for this is to enable execution of the focal point of epilepsy to a maximum, while reducing the damage to the speech area and the visual area to a minimum, by accurately identifying the position of the speech area and the visual area, thus to improve the treatment outcome.

On the other hand, to accurately identify the areas where the relative variations of hemoglobin concentration greatly changes (the focal point of epilepsy), it is necessary to identify the measuring point having the largest relative variations of hemoglobin concentration and the areas around it having large relative variations. However, when the relative variations of hemoglobin concentration are displayed with colors, as in the conventional optical measurement apparatus for a living body, the area to be examined might depend on the difference in the examiner's sensitivity to colors. Therefore, the provision of a display method by which the examiner can objectively identify the area where the relative variation of hemoglobin concentration is greatest has been desired.

An object of the present invention is to provide a technique by which the examiner can objectively identify the area to be examined in diagnosis using an optical measurement apparatus for a living body.

Another object of the present invention is to provide a technique by which the efficiency of diagnosis using an optical measurement apparatus for a living body can be improved.

The above-described and other objects and novel features of the invention will be revealed in the description provided in this specification and from the attached drawings.

SUMMARY OF THE INVENTION

To achieve the above-described objects, the present invention provides an optical measurement apparatus for examination of a living body, which apparatus is constituted of light transmitting means for transmitting light to a plurality of positions in the area of a living body under examination; light detecting means for detecting, at a plurality of positions in the area under examination, light which has been transmitted by the light transmitting means and has passed through the living body; load applying means for applying to the living body a load to which the living body responds; means for generating signals representing an intensity change of transillumination detected by the light detecting means at measuring points which are determined based on a positional relation between each of the light transmitting means and the light detecting means, during both a period in which the load is applied to the living body and a period in which the load is not being applied; means for converting time variations of at least one signal among two signals detected by the light detecting means and time variations of the light signal at each measuring point into time variations of hemoglobin concentration; means for calculating the time variations of hemoglobin concentration calculated at the measuring points, determined on the basis of the positional relation between each of the light transmitting means and the light detecting means; and display control means for displaying graphs of the time variations of hemoglobin concentration in correspondence with the positional relation between each of the light transmitting means and the light detecting means.

The optical measurement apparatus for a living body, as described above, includes means for selecting and classifying graphs displayed on display means by the display control means into a plurality of groups.

The optical measurement apparatus for a living body according to the present invention further includes means for distinguishably displaying the respective graphs of the groups to be displayed, classified by the selecting means.

Further, the optical measurement apparatus for a living body desirably includes means for displaying on the display means a particular group of graphs, among the plurality of groups of graphs classified by the selecting means. Also, the apparatus desirably includes means for averaging measured values of the respective groups of graphs classified by the selecting means, and means for displaying on the display means data of the average values of the respective groups of graphs. Further, the apparatus desirably includes means for converting the average values calculated by the averaging means into data displayed as graphs on the display means.

The optical measurement apparatus for a living body desirably includes means for calculating a correlation between standard data representing characteristics of one selected group and data calculated by the averaging means, and means for displaying a value of the calculated correlation near the displayed graph. Further, it is preferable that the standard data representing the characteristics of one selected group is stored in storing means, and the stored standard data is read out by readout means.

Further, the optical measurement apparatus for a living body desirably includes means for inputting the standard data representing the characteristics of one selected group, and the standard data inputting means desirably includes an operation device for inputting a plurality of coordinate points on a coordinate plane having two axes, for signal intensity and for time, on a screen of the display means, means for calculating by interpolation processing the coordinate points between the respective coordinate points input by the operation device, and means for generating a correlation standard graph from the input coordinate points and the coordinate points calculated by the interpolation processing. Further, the standard data inputting means desirably includes means for converting the signal intensity and the time of the coordinate points input by the operation device into numerical values, and for displaying the values as a chart.

Further, the optical measurement apparatus for a living body desirably includes means for calculating a difference value between the average value of measured values in the period in which the load is applied to the living body and the average value of measured values in the period when the load is not applied to the living body, and means for displaying the difference value calculated by the difference calculating means in the vicinity of the displayed graph.

The optical measurement apparatus for a living body according to the present invention may also take the form described below, so as to achieve the above-described objects. That is, the optical measurement apparatus for a living body may be constituted of a plurality of light-transmitters for transmitting light, which are discretely placed at plural positions on the head of a living body; a plurality of light detectors for detecting light which has been transmitted by the light-transmitters placed discretely on plural positions on the head of the living body and which has passed through the living body, the light detectors being placed alternately with respect to the light-transmitters; load applying means for applying a load to which the living body responds when the load is applied; preliminary measurement means for performing a preliminary measurement during the period when the load is not applied to the living body, in order to measure a standard signal; actual measurement means for performing actual measurement, which has a rest period in which the load is not applied to the living body and a loading period in which the load is applied to the living body by the load applying means, so as to measure a signal representing an intensity change of the transillumination detected by the light detecting means; means for calculating relative variations of the signal measured in the actual measurement with respect to the standard signal by comparing the signal calculated above and the standard signal; and display control means for displaying graphs of the above-calculated relative variations in correspondence with the measuring points determined on the basis of the positional relation between each of the light transmitting means and the light detecting means.

Further, as another form of the present invention, the optical measurement apparatus for a living body may be constituted of light transmitting means for transmitting light to a plurality of positions on the body surface corresponding to the areas to be examined in the living body; light detecting means for detecting optical intensity of the light which has been transmitted by the light transmitting means and which has passed through the living body at the plurality of positions on the surface of the living body; means for converting time variations of the intensity of transillumination detected by the detecting means into time variations of hemoglobin concentration and for producing graph data of this time variations of hemoglobin concentration; and means for displaying the graph data at display positions corresponding to the measured points which are determined on the basis of the positional relation between each of the light transmitting means and the light detecting means.

BEST MODE FOR CARRYING OUT THE INVENTION

Hereinafter, an embodiment of the present invention will be described in detail with reference to the drawings. Incidentally, throughout the drawings, elements having the same function are provided with the same reference numbers, respectively.

Figure 1:
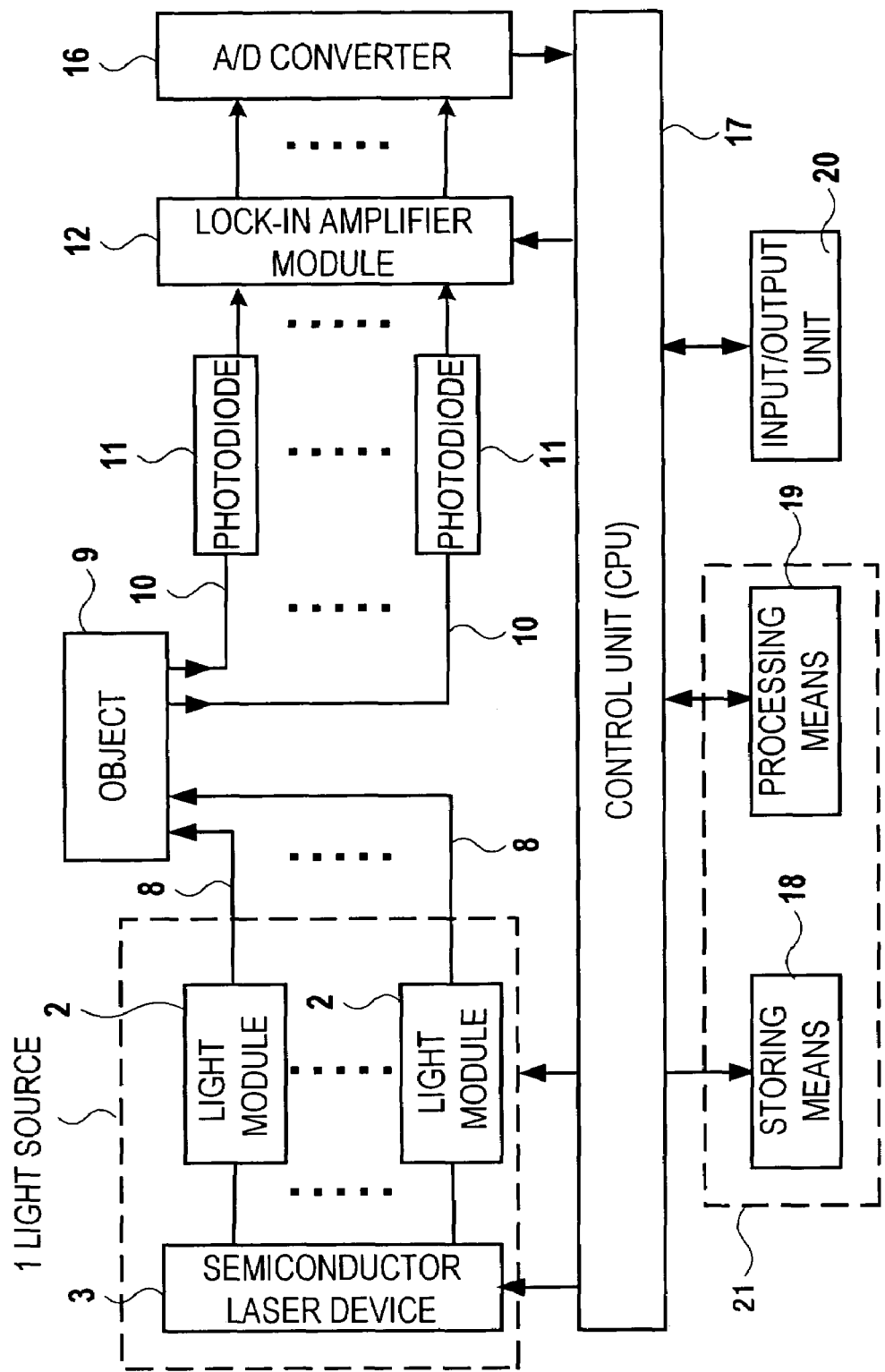
FIG. 1 is a block diagram illustrating an outline of the structure of an optical measurement apparatus for a living body according to one embodiment of the present invention.

FIG. 1 is a block diagram illustrating an outline of the structure of an optical measurement apparatus for a living body according to an embodiment of the invention. In FIG. 1, reference number 1 represents a light source unit, reference number 2 represents light modules, reference number 3 represents semiconductor laser devices, reference number 8 represents optical fibers for illumination, reference number 9 represents an object to be examined, reference number 10 represents optical fibers for detection, reference number 11 represents photodiodes, reference number 12 represents a lock-in amplifier module, reference number 16 represents an A/D converter, reference number 17 represents a control unit (CPU), reference number 18 represents storing means, reference number 19 represents processing means, reference number 20 represents an input/output unit (display control unit), and reference number 21 represents an image generation unit.

Incidentally, among the above-mentioned constituent elements, all elements except the control unit 17, the processing means 19, the input/output unit 20 and the image generation unit 21 are similar to those in the known optical measurement apparatus for a living body, as mentioned in, for example, the above-referenced document 1. Therefore, the following description refers in detail to the control unit 17, the processing means 19, the input/output unit 20, and the image generation unit 21.

The following is a description of the structure and operation of an optical measurement apparatus to be used for speech-dominant hemisphere identification, in which light having various absorptances to oxygenated hemoglobin and deoxygenated hemoglobin is transmitted from the skin surface of the head of an object to be examined to the brain, while activating the speech area of the brain of the object, and relative variations of oxygenated hemoglobin concentration, relative variations of deoxygenated hemoglobin concentration, and relative variations of total hemoglobin concentration are measured from transillumination detected on the skin surface of the head, wherein the optical measurement apparatus has twenty-four measuring channels or measuring positions. However, it is obvious that the stimulation given to the object may be replaced by visual stimulation, pain stimulation, and kinetic stimulation, according to the content of the diagnosis. Further, the region to be measured in accordance with the present invention is not limited to the head, and it may be other portions and it may be also applied to a living body other than a human body. Also, by increasing the number of light-transmitting positions and light-detecting positions, the number of measuring channels can be increased, whereby areas to be measured can be expanded.

Referring to FIG. 1, the light source unit 1 is constituted of the semiconductor laser devices 3 and the light modules 2. The semiconductor laser device 3 is designed to transmit light having plural wavelengths between the visible area and the infrared area, for example, light having the two wavelengths of 780 nm and 830 nm, the number of lasers corresponding to the number of measuring positions. Here, light having the wavelengths of 780 nm and 830 nm is selected because light absorptance to oxygenated hemoglobin and light absorptance to deoxygenated hemoglobin are different. When there are twenty-four measuring positions, as mentioned above, eight units of semiconductor laser devices for transmitting light of 780 nm and eight units of semiconductor laser devices for transmitting light of 830 nm are provided, wherein the total number of semiconductor laser devices is sixteen. To each of the light modules 3, light having the two wavelengths is to be input. Each of the light modules is provided with an oscillator having various oscillation frequencies, and it modulates and outputs the light transmitted by the semiconductor laser devices 2. For example, when light having two wavelengths is used, as described above, light having a modulation frequency of two wavelengths of 780 nm+?fn and 830+?fn, the value of ?fn being varied, is output to each light module. Thus, the number of light modules is eight, being half the number of the semiconductor laser devices. Further, each of the light modules is provided with an optical fiber coupler (not shown) for guiding light produced by modulating light having the two wavelengths of 780 nm and 830 nm to one optical fiber (a light-transmitting optical fiber 8).

Incidentally, the values of the two wavelengths of the light transmitted from the semiconductor laser devices are not limited to 780 nm and 830 nm, and the number of wavelengths is also not limited to two. As a radiation source of the light, a light-emitting diode may be employed, instead of semiconductor laser devices. As the modulation performed in the light module, analog modulation by sine wave and digital modulation by square wave with various time intervals may be employed.

The light produced by mixing two-wavelength light emitted from the light source unit 1 is transmitted to the head to be examined of the object 9 from the tips of eight light-transmitting optical fibers 8 that are connected to the light modules 2, respectively. Each of four light-transmitting optical fibers 8 is fixed to the head of the object 9 by a fixing member (not shown). By putting the optical fibers through this fixing member, the positions of the optical fibers 8 are set at positions different from each other on the head of the object 9. Furthermore, in this embodiment, the tips of the light-transmitting optical fibers 8 and the detecting optical fibers 10 are alternately arranged on a tetragonal lattice. In the above-described structure, the positional relation between the light-transmitting optical fibers 8 and the detecting optical fibers 10, and the modulation frequencies of the light entering the light-transmitting optical fibers 8 are recognized by the control unit 17. Incidentally, a measurement probe is described in detail in the above-referenced document 1.

The living-body transillumination, which has been transmitted from the eight optical fibers 8 and has passed through the head, is collected at ten detecting optical fibers 10 that are fixed on the fixing member. Here, the light transmitted mainly from adjacent light-transmitting optical fibers to the object 9 enters each detecting optical fiber.

The light entering the detecting optical fibers is detected at the photodiodes 11, which serve as light detectors and are connected to the other end of each optical fiber 10. It is preferable to employ known avalanche photodiodes by which optical measurement can be performed with high sensitivity. However, if a light detector other than a photodiode is desired, some other device having a photoelectric conversion function, such as a photo multiplier, may be employed.

The living-body transillumination that is guided to the photodiodes 11 is converted into electric signals (living-body transillumination intensity signals), and a modulating signal corresponding to the light-transmitting point and wavelength are selectively detected at a detection circuit which can selectively detect the modulating signal, such as the lock-in amplifier module 12, consisting of a plurality of lock-in amplifiers. Here, the modulating signal output from the lock-in amplifier module 12 is a signal which has been divided into a living-body transillumination intensity signal of particular wavelength and light-transmitting positions. However, since measurement in this embodiment is performed at twenty-four measuring points using light having two wavelengths, the number of signals to be measured is forty-eight. Therefore, the lock-in amplifier module 12, according to this embodiment, is provided with a total of forty-eight lock-in amplifiers (not shown). Further, when digital modulation is employed, a digital filter or a digital signal processor is used for the modulating signal detection.

The living-body transillumination intensity signals that are output as analog signals from the lock-in amplifier module 12 are respectively converted into digital signals by the A/D converter (analog-digital converter) 16, having forty-eight channels. Each of these signals is a living-body transillumination intensity signal corresponding to each wavelength and light-transmitting point. The above measurement is controlled by the control unit 17.

The living-body transillumination intensity signals that are converted into digital signals are sequentially output to the storing means 18 and the processing means 19. The storing means 18 sequentially stores the living-body transillumination intensity signals.

The processing means 19 calculates the relative variations of oxygenated hemoglobin concentration $\Delta C_{oxy}$ and relative variations of deoxygenated hemoglobin concentration $\Delta C_{deoxy}$ at each measuring point from the living-body transillumination intensity signals measured during the period in which word stimulation is applied, that is, a loading period with respect to standard transillumination intensity signals, being living-body transillumination intensity signals measured during a period referred to as a rest period in which word stimulation is not applied, among the above-input living-body transillumination intensity signals. Then, the processing means 19 displays as a living-body transillumination intensity image, on a display screen of the input/output unit 20, the relative variations of oxygenated and deoxygenated hemoglobin concentration $\Delta C_{oxy}$ and $\Delta C_{deoxy}$, and the relative variations of the total hemoglobin concentration, which is the sum of the relative variations of oxygenated hemoglobin concentration $\Delta C_{oxy}$ and the relative variations of deoxygenated hemoglobin concentration $\Delta C_{deoxy}$. The relative variations of oxygenated hemoglobin concentration $\Delta C_{oxy}$, the relative variations of deoxygenated hemoglobin concentration $\Delta C_{deoxy}$, and the relative variations of total hemoglobin concentration being the sum of the relative variations of oxygenated hemoglobin concentration $\Delta C_{oxy}$ and the relative variations of deoxygenated hemoglobin concentration $\Delta C_{deoxy}$ are displayed separately or in combination. Since the method of calculation of the relative variations of oxygenated hemoglobin concentration and the relative variations of deoxygenated hemoglobin concentration from the living-body transillumination intensity signals at each detection position is mentioned in the above-referenced document 1, a detailed description thereof is omitted.

On the other hand, if a graphical representation of living-body transillumination intensity signals at each measuring position is commanded from a console (not shown), which is connected to the input/output unit 20, the processing means 19, according to this embodiment, displays at a position corresponding to each measuring position a graph of variations of living-body transillumination intensity signals equivalent to the relative variations of oxygenated hemoglobin concentration or deoxygenated hemoglobin concentration, or the total hemoglobin concentration, instead of displaying these relative variations. Here, if a representation of the correlation between the living-body transillumination intensity signals at each measuring position is commanded from the console, the processing means 19 calculates a correlation value from the living-body transillumination signals at each measuring position and the predetermined standard values stored in the storing means 28, and it displays a numerical value or a graph of the thus obtained correlation value. This allows an examiner to objectively determine the location of every kind of function area, which has been conventionally determined by the examiner's subjective reading of the display.

Figure 2:
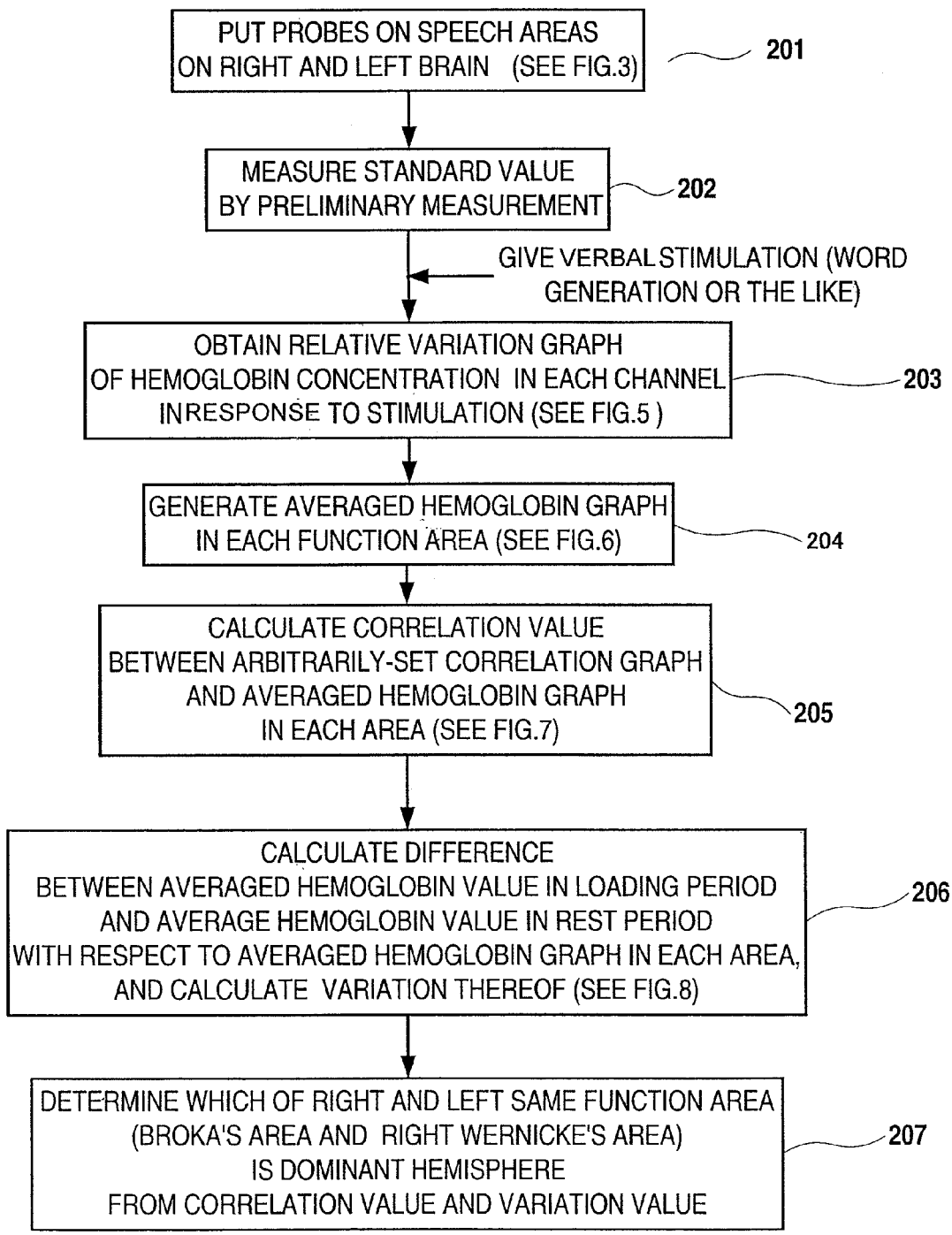
FIG. 2 is a flow chart showing the process of the living-body optical measurement using an optical measurement apparatus for a living body according to this embodiment.

FIG. 2 is a flow chart illustrating the process of optical measurement in the optical measurement apparatus for a living-body according to this embodiment. Hereinafter, the operation in a graphical representation and measuring area setting will be described with reference to FIG. 2. However, as mentioned above, the flow chart shown in FIG. 2 is suitable for so-called speech-dominant-hemisphere identification diagnosis, in which the brain area which is dominant in speech function is identified in the right brain and in the left brain, when the object to be measured is a human body (the object 9).

First, the light-transmitting optical fibers 8 and detecting optical fibers 10 are arranged by the examiner, such that an area referred to as a speech area, which is clinically known, is within the measuring area (step 201).

Figure 3:
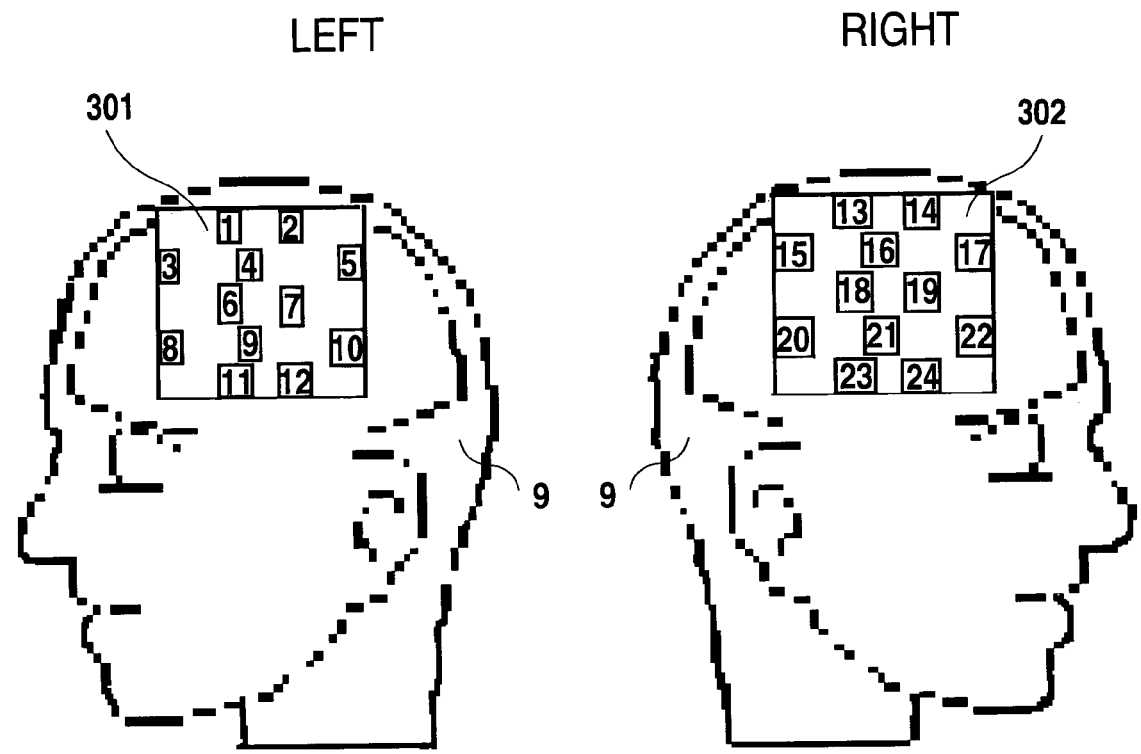
FIG. 3 is a diagram showing positions of measuring points on the right brain and the left brain.
Figure 4:
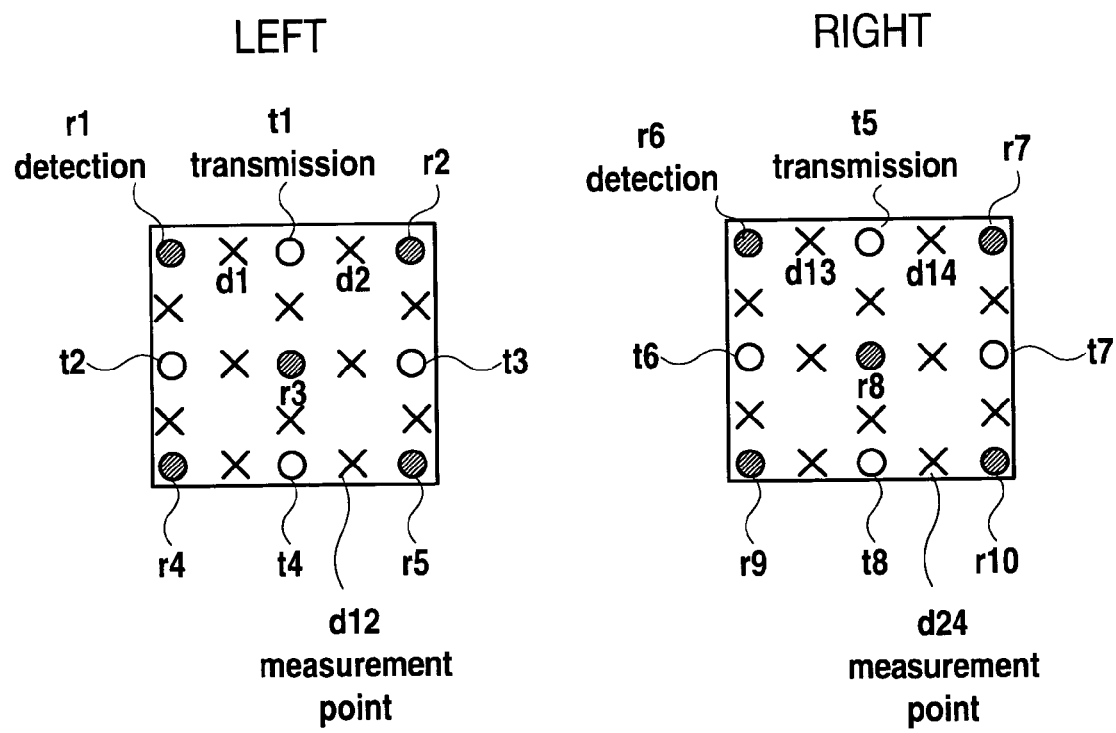
FIG. 4 is a diagram showing fixing points of optical fibers for illumination and for detection by which the measuring points shown in FIG. 3 are determined.

Here, as shown in FIG. 3 and FIG. 4, eight light-transmitting optical fibers 8 and ten detecting optical fibers 10 are placed on the head of object 9, such that first to twelfth measuring positions are set on the left brain of object 9, and thirteenth to twenty-fourth measuring points are set on the right brain. That is, four light-transmitting optical fibers t1 to t4 and five detecting optical fibers r1 to r5 are placed on the left-brain side, and four light-transmitting optical fibers t5 to t8 and five detecting optical fibers r6 to r10 are placed on the right-brain side. When the light-transmitting optical fibers and the detecting optical fibers are thus placed on the object 9, twelve points d1 to d12, which are intermediate positions between the light-transmitting optical fibers and the detecting optical fibers, are the measuring positions on the right-brain side, and twelve points of intermediate positions d13 to d24 are similarly measuring positions on the left-brain side.

After setting the optical fibers as described above, the object 9 is kept in bed, and a preliminary measurement is performed. A standard value for calculating relative variations of oxygenated hemoglobin concentration, deoxygenated hemoglobin concentration, and the total hemoglobin concentration in the actual measurement is here measured.

After the preliminary measurement is completed, the actual measurement is started. The actual measurement is the combination of measurement in the rest period and measurement in the loading period. In the actual measurement according to this embodiment, a task consisting of the measurement in the rest period, the subsequent measurement in the loading period, and the measurement in the rest period subsequent to the loading period is repeatedly and continuously performed plural times (step 202).

When light is transmitted from the light-transmitting optical fibers 8 to the object 9, living-body transillumination, which has passed through the object 9 and is modified according to the presence or absence of verbal stimulation, enters one end of the detecting optical fibers 10. The living-body transillumination is sent to the apparatus body by detecting optical fibers 10, and it is converted into electric signals at the photodiodes 11. After that, the living-body transillumination intensity signals are input to the lock-in amplifier modules 12 and are divided there into living-body transillumination intensity signals of each wavelength, converted into digital signals at the A/D converter 16, stored to the storing means 18, and output to the processing means 109.

Figure 5:
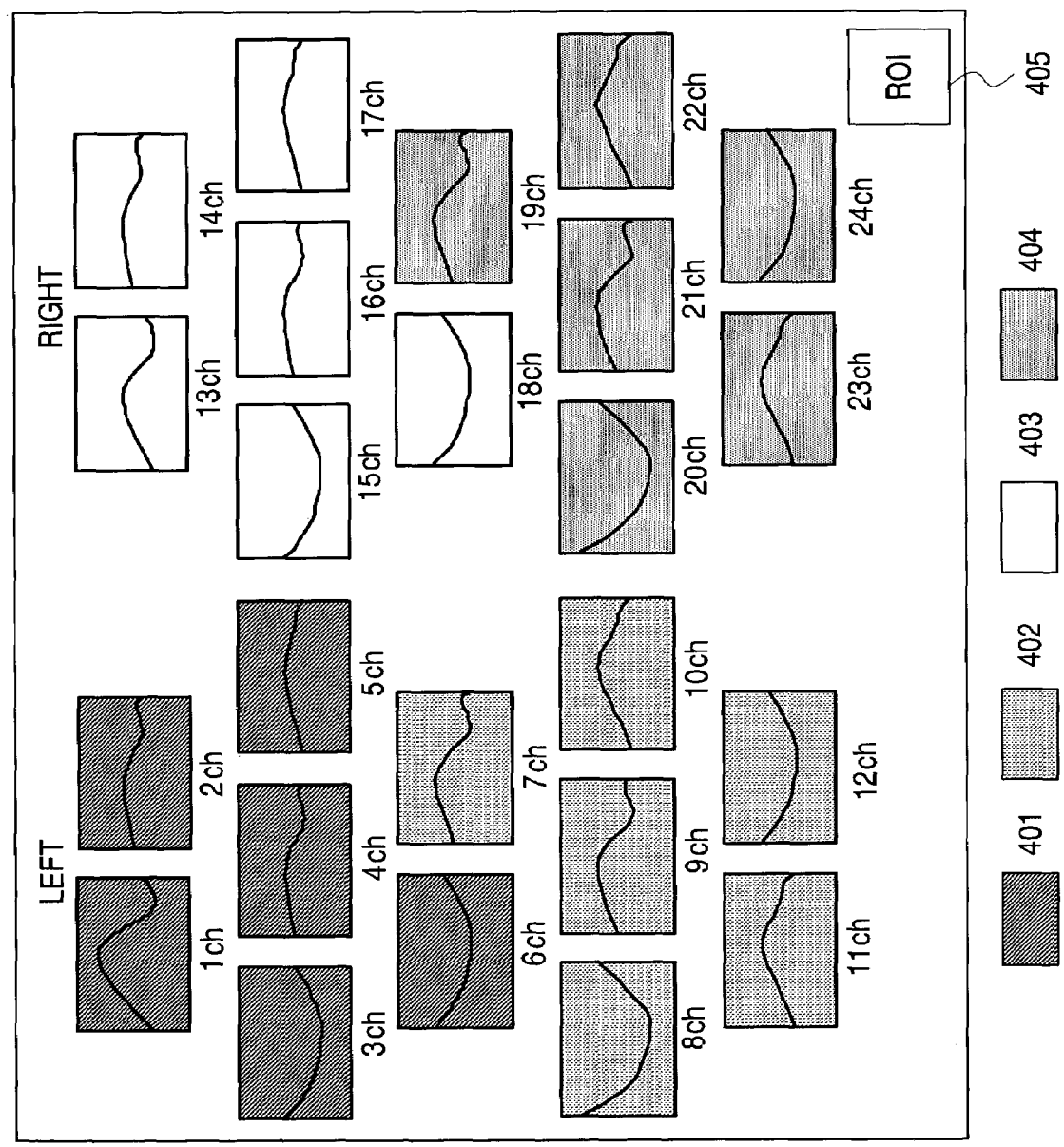
FIG. 5 is a diagram showing one example of displaying graphs representing relative variations of measured hemoglobin concentration.

Adding means in the processing means 19 first adds the living-body transillumination intensity signals which are input from the A/D converter 16 or read out from the storing means 18 as many times as a task number that is determined in advance, based on the time of the start of loading or the end of loading, in the same manner as, for example, when calculating the relative variations of hemoglobin concentration. Next, the adding means averages the added living-body transillumination intensity signals, whereby the level of noise caused by the measurement is reduced. The thus obtained living-body transillumination intensity signals (average values) are compared with the standard values and relative variations with respect to the standard values are calculated, and the relative variations are output to the display device of the input/output unit 20 in accordance with the instruction from the control unit 17. The outputs are used to form graphs representing relative variations of hemoglobin concentration in twenty-four channels corresponding to the 1-24 measuring positions, as shown in FIG. 5, and the graphs are displayed on a screen of the display device, such that the positional relation between the measuring positions can be understood by the examiner (step 203).

Further, only a graph selected in advance from the graphs of living-body transillumination intensity signals can be displayed on the screen of the display device connected to the input/output unit 20, whereby the visibility of the graphs on the display screen may be improved. Incidentally, the representations of the 1 ch-24ch shown in FIG. 4 respectively correspond to the channel numbers indicating the measuring positions in FIG. 3. In this embodiment, the control unit 17 is designed to be able to control ON/OFF operation of display of the channel numbers through an input operation from the console (not shown). Thus, the graph of each of the measuring points may be easily identified.

Further, the processing means 19 sets the relative display positions of the graphs corresponding to the measuring positions set on the object 9 according to the positional information of the measuring positions output from the control unit 17, whereby the examiner can viscerally understand the positional relation between the measuring positions and the graphs. A select button for identifiably displaying the graphs for one function area (the speech area in this embodiment) is provided on the console. By controlling the select button appropriately, the work of the examiner in referring to the displayed graphs and in selecting the graphs belonging to the same function area can be reduced.

In the process of selecting one function area, taking as an example the case where the measuring positions d1-d6 are set as the same function area, the left Broca's area, the examiner first selects graphs of the measuring positions d1-d6, as represented on the display. Next, the selecting-operation is carried out by selecting an ROI icon 405 (cf. FIG. 5) so as to set the areas selected by the examiner as the same function area. Thus, the living-body transillumination intensity signals at the measuring positions d1-d6 are set as living-body transillumination intensity signals of the same function area. The selecting operation at this time is such that, for example, the examiner inputs an instruction using a pointing device or the like (not shown) that is connected to the input/output unit 20, and graph selecting means integrated in the processing means 19 sequentially selects graphs to be set as the same function area. Following the graph selecting operation, the examiner selects the ROI icon 405 on the screen, and the measuring areas corresponding to the selected graphs are registered as the same function area. As the measuring positions that are selected to be the same function area are registered, the graphs of the selected same function area are displayed with hue information on, for example, the frame of the graph, the background, the broken lines, the channel numbers or the like, so as to be discernable from graphs of other function areas.

Further, relative variations of hemoglobin concentration in the selected measuring areas are used as one group of data by the above-described selecting operation in the optical measurement apparatus for a living body according to this embodiment, whereby a predetermined processing, to be described below, is enabled. Incidentally, in this embodiment, the measuring positions d1-d6 are set to be the left Broca's area, the measuring positions d7-d12 are set to be the left Wernicke's area, the measuring positions the d13-d18 are set to be the right Broca's area, and the measuring positions d19-d24 are set to be the right Wernicke's area.

After the area setting is completed, the processing means 19 averages the living-body transillumination intensity signals in the respective measuring positions set to be the same function area, and sets the thus obtained value as the living-body transillumination intensity signal of that function area. Next, the processing means 19 generates graphs of the respective function areas from the living-body transillumination intensity signals acquired by averaging with the same process as the above graphing process of the respective measuring positions, and it outputs the thus obtained graphs to the input/output unit 20. Thus, as shown in FIG. 6, averaged hemoglobin graphs 501-504 of the respective same function areas are displayed on the screen (step 204).

Next, the processing means 19 calculates correlation values between the averaged hemoglobin graphs 501-504 and a preset or examiner-set standard graph (hereinafter referred to as a correlation graph), and the thus obtained correlation values are displayed in display areas 601-604 below the averaged hemoglobin graphs 501-504 (step 205).

Figure 6:
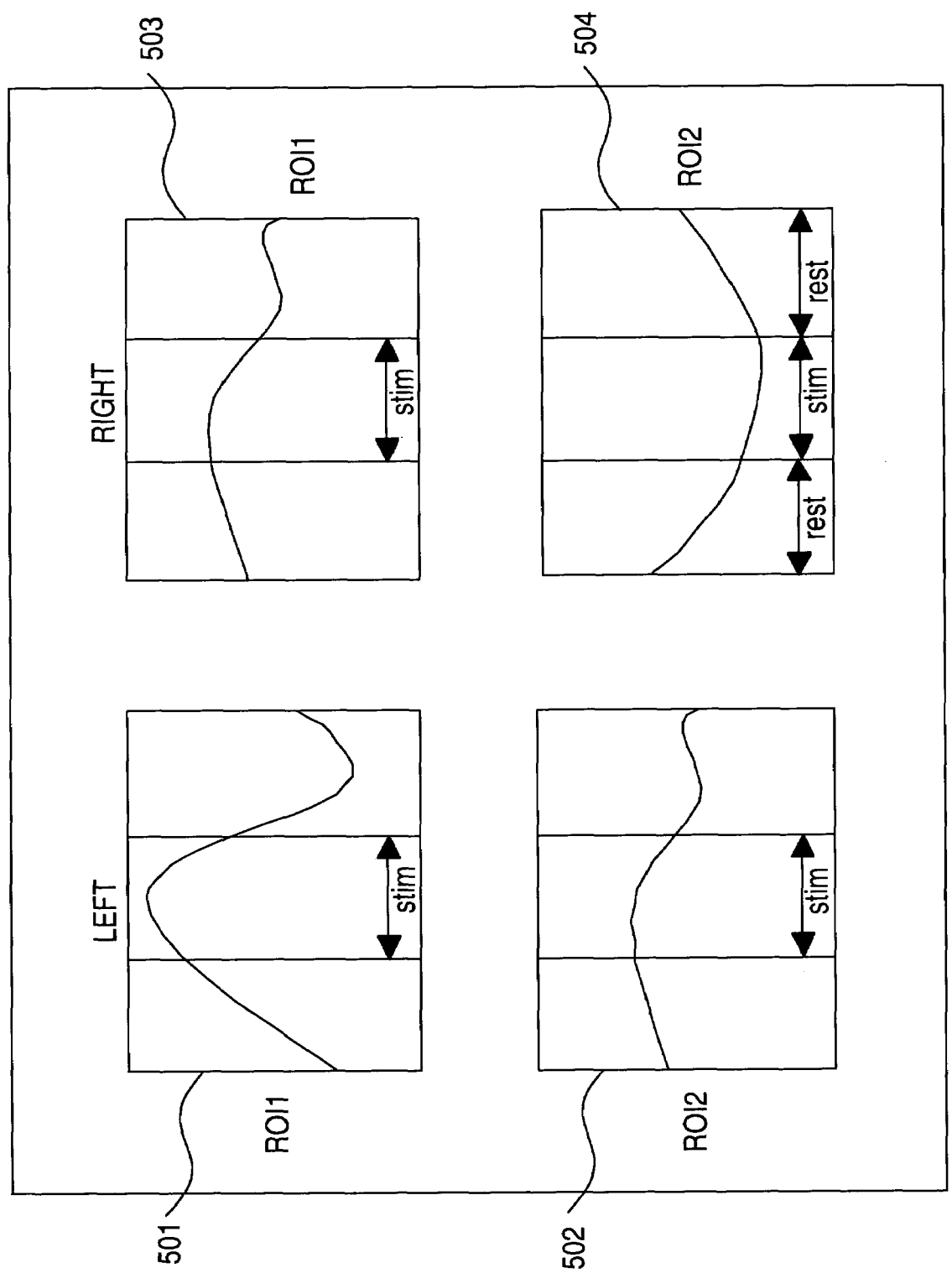
FIG. 6 is a diagram showing one example of displaying graphs representing relative variations of hemoglobin concentration in the same function area.
Figure 7:
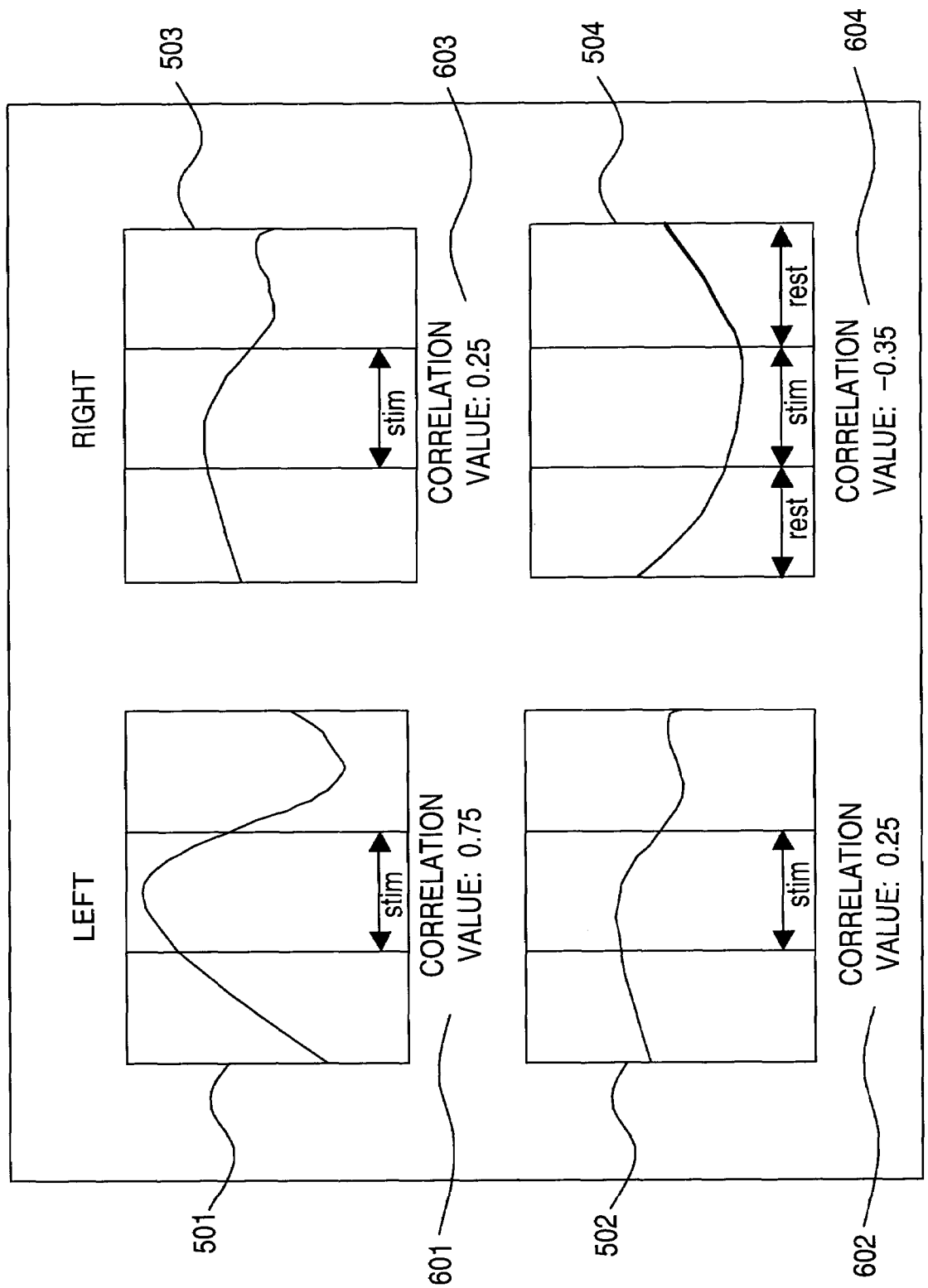
FIG. 7 is a diagram showing one example of a display in which relative variations of hemoglobin concentration in the same function area and correlation values on correlation graphs are represented together with the graph.

The state of display at this point is shown in FIG. 6. As is clear from FIG. 6, the optical measurement apparatus for a living body, according to this embodiment, enables easy determination of the similarity between the averaged hemoglobin graphs 501-504 obtained in the step 204 and the preset correlation graph. Therefore, when a standard graph of the speech area, which dominantly changes in accordance with verbal stimulation, is set as the correlation graph, the examiner can easily and objectively identify the speech area by comparing the correlation values displayed in the vicinity of the graphs 501-504. Although the period in which a correlation value is obtained is set as the entire period for one task in this embodiment, the embodiment is not limited thereto. For example, only the correlation values of the loading period may be calculated. Further, in this embodiment, predetermined graphs or examiner-set graphs are the standard graphs for correlation calculations, but the embodiment is not limited thereto. For example, the living-body transillumination intensity signals of the respective measuring areas shown in FIG. 5 may be set as the standard graphs. The structure for setting the living-body transillumination intensity signals of the respective measuring areas as the standard graphs is such that an icon for selecting standard graphs is provided on the display screen, as the above-mentioned ROI icon 405 is provided, and selected graphs of living-body transillumination intensity signals are set as the standard graphs by operating this icon. In this manner, the examiner can easily select the standard graphs.

The processing means 19 has a function of calculating the difference between the signals in the loading period and those in the rest period in the same manner as calculation of the living-body transillumination intensity signals at the respective measuring positions, after dividing the living-body transillumination intensity signals calculated in the step 204 by the living-body transillumination intensity signals in the period of applying verbal stimulation (loading period) and by the living-body transillumination intensity signals in the rest period (rest). The difference values obtained by this difference calculation function are displayed under the respective averaged hemoglobin graphs 501-504 (step 206).

Figure 8:
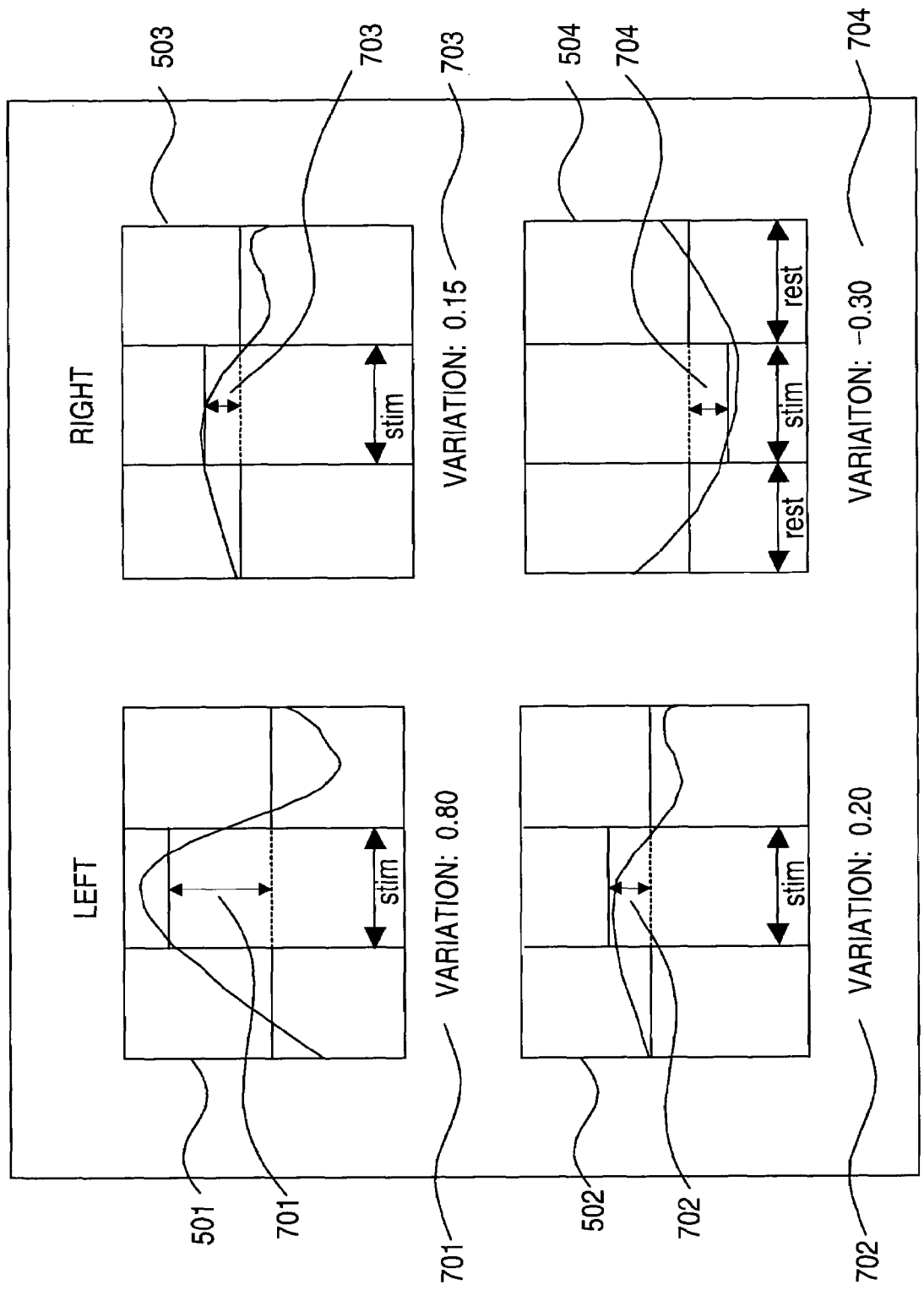
FIG. 8 is a diagram showing one example of displaying difference values between the loading period and the rest period along with graphs representing relative variations of hemoglobin concentration in the same function area.

FIG. 8 shows the state of display at this point. As is clear from FIG. 8, numerical values of relative variations of the same function areas are displayed in display areas 701-704, whereby the area which dominantly changes in response to verbal stimulation can be objectively identified. As a result, the efficiency of a speech dominant-hemisphere identification diagnosis carried out by the examiner may be improved. Incidentally, the difference values calculated in this step may be the relative variations of the total hemoglobin concentration, which is used when generating the living-body transillumination intensity image. The above-described series of operations in the processing means 19 is executed by software installed in the control unit 17.

Figure 9:
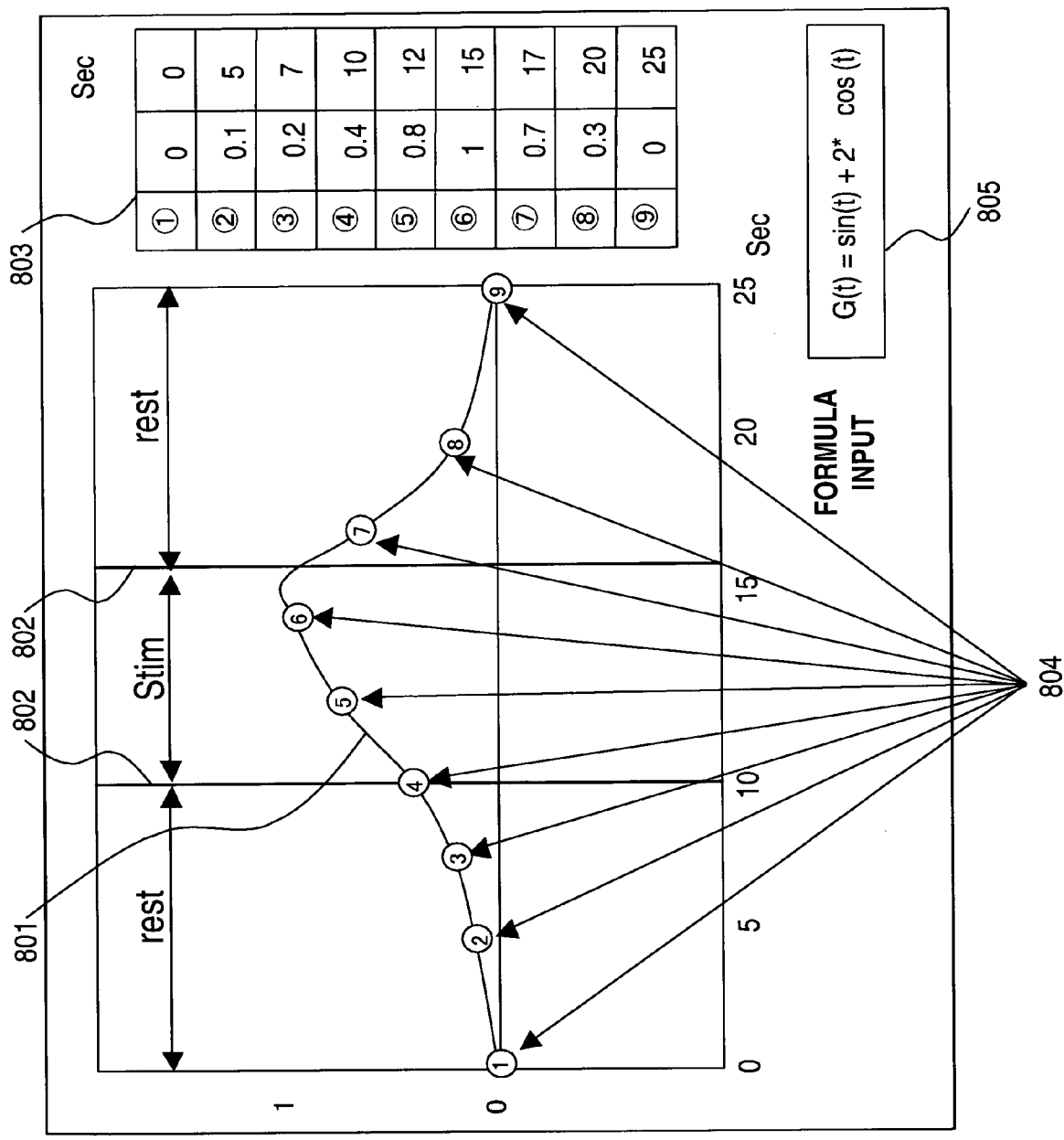
FIG. 9 is a diagram illustrating a process of setting a correlation graph in the optical measurement apparatus for a living body according to the embodiment of the present invention.

FIG. 9 is a diagram showing the setting process of the correlation graph in the optical measurement apparatus for a living body according to this embodiment. Hereinafter, the setting process of the correlation graph in the optical measurement apparatus for a living body according to this embodiment will be described with reference to FIG. 9.

As shown in FIG. 9, in this embodiment, nine variation points 804 are provided in order to form a correlation graph 801 during the loading period and the rest periods, which are set before and after the loading period. On the setting screen of the correlation graph 801, as shown in FIG. 9, the processing means 19 performs spline interpolation processing between the respective variation points 804 to form the correlation graph 801 after the examiner sets the positions (the signal-intensity direction and the time-axis direction) of the respective variation points 804. Here, the positions of the respective variation points 804 on the time axis and the signal intensity axis are displayed in a chart 803 on the same screen so as to allow the examiner to set the correlation graph 801. Especially, when the coordinate values in the chart 803 showing coordinate positions of the respective variation points 804 are modified, this modification is promptly reflected to the correlation graph 801 in this embodiment, whereby the setting of the correlation graph 801 can be easily and effectively performed. Further, bars 802 indicating a starting point and an ending point of the loading period are provided within the display area of the correlation graph 801. By using the bars 802 as indication lines for setting the correlation graph 801, the examiner can set the correlation graph more easily. Incidentally, the interpolation processing by the processing means 19 need not be the spline interpolation, but the interpolation processing due to other interpolation calculations, such as linear interpolation, may be employed. The number of variation points 804 is not limited to nine.

Further, in this embodiment, an area in which a formula for setting the form of the correlation graph 801 (a formula input area) is provided on the same screen, wherein the correlation graph can be set according to a formula which is directly input by the examiner. Here, the formula to be set is displayed in the formula display area 805. The above-described correlation processing is also executed by the software installed in the control unit 17.

According to the above-described embodiment, the input/output unit 20 generates a graph in accordance with average values output from the processing means 19, the graph is displayed on the display device connected to the input/output unit 20, and the difference values corresponding to the respective graphs are displayed in the vicinity of the respective graphs by the input/output unit 20, whereby the examiner can objectively understand the variations of the transillumination. Therefore, the speech area can be objectively determined (step 207).

Further, correlation values of the function areas that are more suitable for diagnosis are calculated by calculating correlations with respect to the standard values stored in storing means 18, and the examiner can perform diagnosis with reference to the result thereof, so that the diagnostic efficiency is improved.

A detailed description of the present invention according to an embodiment of the present invention has been provided. However, the invention is not limited to this embodiment. Various changes may be made without departing from the scope of the invention.

The following is a brief description of the effects brought about by the representative elements of the invention laid open in this application:

(1) Since the examiner can objectively understand variations of the transillumination, he or she can objectively determine the speech area to be examined;

(2) Since the examiner can observe intensity variations of the transillumination within measurement areas determined by the arrangement of a plurality of light-transmitting and detecting optical fibers placed on the object, he or she can objectively understand the variations of the transillumination in a particular function area, and can perform a determination on the function area to be examined. Therefore, the diagnostic efficiency is improved.

(3) The examiner can easily understand the result of comparison between variations of the transillumination intensity in each measurement area or/and each group and variations of the transillumination intensity from the standard graph, whereby the diagnostic efficiency is further improved.

What is claimed is:

1. An optical measurement apparatus for examination of a living body comprising:
   light transmitting means for transmitting light to a plurality of positions in an area being examined within a living body;
   light detecting means for detecting light which has been transmitted by said light transmitting means and has passed through the living body at a plurality of positions in the area being examined;
   means for calculating signals representing the intensity change of transillumination detected by said light detecting means at measuring points that are determined based on a positional relation between said light transmitting means and said light detecting means, during a period in which a load is applied to the living body and periods in which the load is not applied;
   means for calculating time variations of at least one signal among two signals calculated at the measuring points that are determined based on the positional relation between each of said light transmitting means and said light detecting means;
   means for converting the calculated time variations of the light signal at each measuring point into time variations of hemoglobin concentration; and
   display control means for displaying graphs of the calculated time variations of hemoglobin concentration in correspondence with the positional relation between each of said light transmitting means and said light detecting means; and
   means for selecting and classifying graphs displayed by said display control means on display means so as to display plural groups of graphs.

2. An optical measurement apparatus for examination of a living body according to claim 1, further comprising means for displaying each group of graphs that are classified by said selecting means so as to be distinguishable from other groups of graphs.

3. An optical measurement apparatus for examination of a living body according to claim 1, comprising means for displaying only one particular group of graphs among the plural of groups of graphs selected and classified by said selecting means.

4. An optical measurement apparatus for examination of a living body according to claim 1, comprising means for averaging measured values of signals of the respective groups of graphs classified by said selecting means and means for displaying to said display means the average data of the groups of graphs averaged by said averaging means.

5. An optical measurement apparatus for examination of a living body according to claim 4, wherein said averaging means includes means for converting the calculated average values into data of graphs to be displayed to said display means.

6. An optical measurement apparatus for examination of a living body according to claim 5, comprising means for calculating a correlation between standard data representing characteristics of one selected group of graphs and data calculated by said averaging means, and means for displaying values representing the calculated correlation in the vicinity of the displayed graphs.

7. An optical measurement apparatus for examination of a living body according to claim 6, comprising means for storing the standard data representing characteristics of one selected group of graphs, and means for reading out the stored standard data.

8. An optical measurement apparatus for examination of a living body according to claim 6, comprising means for inputting the standard data representing characteristics of one selected group of graphs.

9. An optical measurement apparatus for examination of a living body according to claim 8, wherein said standard data inputting means includes an operation device for inputting, on a screen of said display means, a plurality of coordinate points on a coordinate having two axes indicating signal intensity and time, means for calculating, by interpolation processing, a coordinate points located plane between the respective coordinate points input by this operation device, and means for generating a correlation standard graph from the input coordinate points and the coordinate points calculated by the interpolation processing.

10. An optical measurement apparatus for examination of a living body according to claim 9, wherein said standard data input means includes means for converting signal intensity and time of the coordinate points input by said operation device into numerical values, and displaying the numerical values in the form of a chart.

11. An optical measurement apparatus for examination of a living body according to claim 5, comprising means for calculating a difference value between an average value of the measured values in a period in which a load is applied to the living body and an average value of measured values in a period in which the load is not applied to the living body, and means for displaying the difference value calculated by this difference value calculating means in the vicinity of each graph display.

12. An optical measurement apparatus for examination of a living body comprising:
   a plurality of light-transmitters adapted to be arranged at positions on the head of a living body for transmitting light;
   a plurality of light detectors, adapted to be arranged at positions on the head of the living body alternately with respect to said light-transmitters, for detecting light which has been transmitted by said light-transmitters and has passed through the living body;
   load applying means for applying stimulation to which the living body responds when applied;
   preliminary measurement means for performing preliminary measurement in a state where a load is not applied to the living body so as to measure a standard signal;
   actual measurement means for performing actual measurement having rest periods in which a load is not applied to the living body and a loading period in which a load is applied to the living body by said load applying means, and measuring signals representing an intensity change of transillumination detected by said light detectors;

means for calculating relative variations of measured signals in the actual measurement with respect to the standard signal by comparing the above-calculated signals and the standard signal;

display control means for displaying graphs of the above-calculated relative variations in correspondence with the positions of each of said light-transmitters and said light detectors; and means for selecting and classifying graphs displayed by said display control means on display means so as to display plural groups of graphs.

13. An optical measurement apparatus for examination of a living body according to claim 12, wherein said light light-transmitters and said light detectors are arranged at positions corresponding to brain function areas of the living body.

14. An optical measurement apparatus for examination of a living body according to claim 12, wherein said preliminary measurement means repeatedly measures signals a plural number of times with a predetermined period in a state where the living body reclines, calculates the average value thereof, and stores this average value in storing means as a standard value.

15. An optical measurement apparatus for examination of a living body according to claim 12, wherein said actual measurement means sequentially executes measurement in the rest period and measurement in the loading period a plural number of times, averages measured signals at each measuring period with elapsed time, and stores the thus calculated average values as measured values.

16. An optical measurement apparatus for examination of a living body comprising:

a plurality of light-transmitters adapted to be arranged at positions on the head of a living body for transmitting light;

a plurality of light detectors, adapted to be arranged at positions on the head of the living body alternately with respect to said light-transmitters, for detecting light which has been transmitted by said light-transmitters and has passed through the living body;

load applying means for applying to the living body a load to which the living body responds when applied;

preliminary measurement means for performing preliminary measurement in a state where a load is not applied to the living body so as to measure a standard signal;

actual measurement means for executing actual measurement consisting of a rest periods where the load is not applied to the living body and a loading period where the load is applied by said load applying means, and for generating signals representing an intensity change of transillumination detected by said light detectors;

means for calculating relative variations of measured signals in the actual measurement with respect to the standard signal by comparing the above-calculated signals and the standard signal;

display control means for displaying graphs of the calculated relative variations on display means in correspondence with the measuring points that are determined based on the positional relation between each of said light-transmitters and said light detectors; and means for selecting and classifying graphs displayed by said display control means on display means so as to display plural groups of graphs.

17. An optical measurement apparatus for examination of a living body comprising:

light transmitting means for transmitting light to a plurality of positions on the body surface corresponding to areas to be examined within the living body;

light detecting means for detecting the light intensity of light which has been transmitted by said light transmitting means and has passed through the living body at a plurality of positions on the body surface of the living body;

means for converting time variations of the intensity of transillumination detected by said light detecting means when brain functions of the living body are activated into time variations of hemoglobin concentration, and making graph data of the time variations of hemoglobin concentration;

displaying control means for displaying graphs based on the graph data at display positions corresponding to the measuring positions that are determined based on the positional relation between said light transmitting means and said light detecting means; and means for selecting and classifying graphs displayed by said display control means on display means so as to display plural groups of graphs.

* * * * *